(12) United States Patent
Niazimbetova et al.

(10) Patent No.: US 8,262,895 B2
(45) Date of Patent: *Sep. 11, 2012

(54) PLATING BATH AND METHOD

(75) Inventors: Zukhra I. Niazimbetova, Westboro, MA (US); Maria Anna Rzeznik, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 297 days.

This patent is subject to a terminal disclaimer.

(21) Appl. No.: 12/661,311

(22) Filed: Mar. 15, 2010

(65) Prior Publication Data

US 2011/0220513 A1   Sep. 15, 2011

(51) Int. Cl.
 *C08F 2/10* (2006.01)
 *C08G 59/14* (2006.01)
 *C23C 18/38* (2006.01)
 *C25D 3/38* (2006.01)

(52) U.S. Cl. .................. 205/297; 106/1.26; 252/183.11; 427/487; 528/117

(58) Field of Classification Search ........................ None
See application file for complete search history.

(56) References Cited

U.S. PATENT DOCUMENTS

| | | | |
|---|---|---|---|
| 2,640,037 A | 5/1953 | Parry et al. | |
| 3,533,985 A | 10/1970 | Lantz et al. | |
| 3,756,984 A | 9/1973 | Klaren et al. | |
| 3,843,667 A | 10/1974 | Cupery et al. | |
| 3,954,575 A | 5/1976 | Yanagida et al. | |
| 4,038,171 A | 7/1977 | Moss et al. | |
| 4,045,306 A | 8/1977 | Senge et al. | |
| 4,066,625 A | 1/1978 | Bolger | |
| 4,116,900 A | 9/1978 | Belanger | |
| 4,169,772 A | 10/1979 | Lowery et al. | |
| 4,211,725 A | 7/1980 | Kluger et al. | |
| 4,397,717 A | 8/1983 | Acimovic et al. | |
| 4,436,892 A | 3/1984 | Zondler et al. | |
| 4,536,261 A | 8/1985 | Popescu | |
| 4,730,022 A | 3/1988 | Willis | |
| 4,792,383 A | 12/1988 | Willis | |
| 4,845,234 A | 7/1989 | Schneider et al. | |
| 4,861,442 A | 8/1989 | Nishihama et al. | |
| 5,026,872 A | 6/1991 | Kohli | |
| 5,175,219 A | 12/1992 | Burba et al. | |
| 5,607,570 A | 3/1997 | Rohbani et al. | |
| 6,518,182 B1 | 2/2003 | Ishikawa et al. | |
| 6,610,192 B1 | 8/2003 | Step et al. | |
| 6,800,188 B2 | 10/2004 | Hagiwara et al. | |
| 7,005,055 B2 * | 2/2006 | Kumagai et al. | 205/296 |
| 7,128,822 B2 | 10/2006 | Wang et al. | |
| 7,374,652 B2 * | 5/2008 | Hayashi et al. | 205/125 |
| 7,510,639 B2 | 3/2009 | Wang et al. | |
| 7,662,981 B2 | 2/2010 | Wang et al. | |
| 2002/0062990 A1 | 5/2002 | Kikuchi et al. | |
| 2005/0166790 A1 * | 8/2005 | Urata et al. | 106/1.18 |
| 2006/0016693 A1 * | 1/2006 | Wang et al. | 205/291 |
| 2006/0135584 A1 | 6/2006 | Imori et al. | |
| 2007/0007143 A1 | 1/2007 | Hayashi et al. | |
| 2010/0326838 A1 * | 12/2010 | Hartmann et al. | 205/236 |
| 2011/0220512 A1 | 9/2011 | Niazimbetova et al. | |
| 2011/0220514 A1 | 9/2011 | Niazimbetova et al. | |

FOREIGN PATENT DOCUMENTS

| | | | |
|---|---|---|---|
| EP | 0 024 119 A1 | 2/1981 | |
| EP | 0 087 790 A1 | 9/1983 | |
| EP | 0 906 927 A1 | 4/1999 | |
| EP | 1 619 274 A2 | 1/2006 | |
| EP | 1 731 545 A1 | 12/2006 | |
| EP | 1 741 804 A1 | 1/2007 | |
| EP | 1 939 935 | 7/2008 | |
| EP | 2 130 948 A1 | 12/2009 | |
| EP | 2130948 A1 * | 12/2009 | |
| GB | 1 279 207 A | 6/1972 | |
| GB | 1 585 611 A | 3/1981 | |
| GB | 2 315 269 A | 1/1988 | |
| JP | 61 286369 | 12/1986 | |
| JP | 3 277631 A | 12/1991 | |
| JP | 7 228572 A | 8/1995 | |
| JP | 2008 266722 A | 11/2008 | |
| RU | 535 301 A1 | 11/1976 | |
| SU | 535 301 A1 | 11/1976 | |
| SU | 1 743 158 A1 | 2/1998 | |

OTHER PUBLICATIONS

IPC-TM-650 Test Methods Manual; IPC Association Connecting Electronics Industries; May 2004; pp. 1-2.
European Search Report of corresponding European Application No. 11 15 8233.
W. Francisco et al.; "Study of the mechanism of action of additional substances in zincate electrolytes"; Powloki Ochronne, 1978, vol. 30, Issue 2, Year VI, pp. 8-17.

* cited by examiner

*Primary Examiner* — Robert Sellers
(74) *Attorney, Agent, or Firm* — S. Matthew Cairns

(57) ABSTRACT

Copper plating baths containing a leveling agent that is a reaction product of a certain benzimidazole with a certain epoxide-containing compound that deposit copper on the surface of a conductive layer are provided. Such plating baths deposit a copper layer that is substantially planar on a substrate surface across a range of electrolyte concentrations. Methods of depositing copper layers using such copper plating baths are also disclosed.

11 Claims, No Drawings

PLATING BATH AND METHOD

The present invention relates generally to the field of electrolytic metal plating. In particular, the present invention relates to the field of electrolytic copper plating.

Methods for electroplating articles with metal coatings generally involve passing a current between two electrodes in a plating solution where one of the electrodes is the article to be plated. A typical acid copper plating solution comprises dissolved copper (usually copper sulfate), an acid electrolyte such as sulfuric acid in an amount sufficient to impart conductivity to the bath, and proprietary additives to improve the uniformity of the plating and the quality of the metal deposit. Such additives include accelerators, levelers, and suppressors, among others.

Electrolytic copper plating solutions are used in a variety of industrial applications, such as decorative and anticorrosion coatings, as well as in the electronics industry, particularly for the fabrication of printed circuit boards and semiconductors. For circuit board fabrication, copper is electroplated over selected portions of the surface of a printed circuit board, into blind vias and onto the walls of through-holes passing between the surfaces of the circuit board base material. The walls of a through-hole are first made conductive, such as by electroless metal deposition, before copper is electroplated onto the walls of the through-hole. Plated through-holes provide a conductive pathway from one board surface to the other. For semiconductor fabrication, copper is electroplated over a surface of a wafer containing a variety of features such as vias, trenches or a combination thereof. The vias and trenches are metallized to provide conductivity between various layers of the semiconductor device.

It is well known in certain areas of plating, such as in electroplating of printed circuit boards ("PCBs"), that the use of accelerators and/or levelers in the electroplating bath can be crucial in achieving a uniform metal deposit on a substrate surface. Plating a substrate having irregular topography can pose particular difficulties. During electroplating a voltage drop variation typically will exist along an irregular surface which can result in an uneven metal deposit. Plating irregularities are exacerbated where the voltage drop variation is relatively extreme, that is, where the surface irregularity is substantial. As a result, a thicker metal deposit, termed overplating, is observed over such surface irregularities. Consequently, a metal layer of substantially uniform thickness is frequently a challenging step in the manufacture of electronic devices. Leveling agents are often used in copper plating baths to provide substantially uniform, or level, copper layers in electronic devices.

The trend of portability combined with increased functionality of electronic devices has driven the miniaturization of PCBs. Conventional multilayer PCBs with through-hole interconnect vias are not always a practical solution. Alternative approaches for high density interconnects have been developed, such as sequential build up technologies, which utilize blind vias. One of the objectives in processes that use blind vias is the maximizing of via filling while minimizing thickness variation in the copper deposit across the substrate surface. This is particularly challenging when the PCB contains both through holes and blind vias.

Generally, leveling agents used in copper plating baths provide better leveling of the deposit across the substrate surface but tend to worsen the throwing power of the electroplating bath. Throwing power is defined as the ratio of the hole center copper deposit thickness to its thickness at the surface. Newer PCBs are being manufactured that contain both through-holes and blind vias. Current bath additives, in particular current leveling agents, do not provide level copper deposits on the substrate surface and fill through-holes and/or fill blind vias effectively.

For example, U.S. Pat. No. 7,374,652 (Hayashi et al.) discloses a method of producing level copper deposits by electroplating copper from a copper plating bath containing a leveling agent that is a reaction product of a certain unsubstituted heterocyclic amine with a polyepoxide compound containing an alkyleneoxy linkage. Even with such leveling agents, level and nodule-free copper deposits on substrate surfaces and filled through-holes or blind vias are not always produced. There remains a need in the art for leveling agents for use in copper electroplating baths used in the manufacture of PCBs that provide level copper deposits while not significantly affecting the throwing power of the bath, that is, the bath effectively fills blind vias and through-holes.

The present invention provides a reaction product of one or more benzimidazole compounds with one or more epoxide-containing compounds; wherein at least one benzimidazole compound has the formula

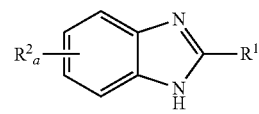

wherein $R^1$ is selected from H, $(C_1-C_6)$alkyl, ar$(C_1-C_6)$alkyl, hydroxy$(C_1-C_6)$alkyl and hydroxy; each $R^2$ is independently selected from $(C_6-C_{18})$aryl, $(C_1-C_6)$alkyl, ar$(C_1-C_6)$alkyl, hydroxy$(C_1-C_6)$alkyl and hydroxy; and a=0-4, provided that a>0 when $R^1$=H. Such reaction products are particularly useful as leveling agents for copper plating baths.

The present invention also provides a copper electroplating bath including: a source of copper ions, an electrolyte, and a leveling agent, wherein the leveling agent is a reaction product of one or more benzimidazole compounds with one or more epoxide-containing compounds; wherein at least one benzimidazole compound has the formula

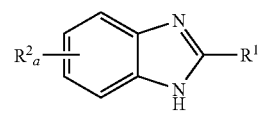

wherein $R^1$ is selected from H, $(C_1-C_6)$alkyl, ar$(C_1-C_6)$alkyl, hydroxy$(C_1-C_6)$alkyl and hydroxy; each $R^2$ is independently selected from $(C_6-C_{18})$aryl, $(C_1-C_6)$alkyl, ar$(C_1-C_6)$alkyl, hydroxy$(C_1-C_6)$alkyl and hydroxy; and a=0-4, provided that a>0 when $R^1$=H.

The present invention further provides a method of depositing copper on a substrate including: contacting a substrate to be plated with copper into a copper electroplating bath including a source of copper ions, an electrolyte, and a leveling agent, wherein the leveling agent is a reaction product of one or more benzimidazole compounds with one or more epoxide-containing compounds; wherein at least one benzimidazole compound has the formula

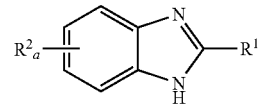

wherein $R^1$ is selected from H, $(C_1-C_6)$alkyl, ar$(C_1-C_6)$alkyl, hydroxy$(C_1-C_6)$alkyl and hydroxy; each $R^2$ is independently selected from $(C_6-C_{18})$aryl, $(C_1-C_6)$alkyl, ar$(C_1-C_6)$alkyl, hydroxy$(C_1-C_6)$alkyl and hydroxy; and a=0-4, provided that a>0 when $R^1$=H; and applying a current density for a period of time sufficient to deposit a copper layer on the substrate.

It has been surprisingly found that the present invention provides copper layers having a substantially level surface across a PCB substrate, even on substrates having very small features and on substrates having a variety of feature sizes. The copper layers deposited according to the present method have significantly reduced defects, such as nodules, as compared to copper deposits from electroplating baths using conventional leveling agents. Further, the present invention effectively deposits copper in through-holes and blind via holes, that is, the present copper plating baths have good throwing power.

As used throughout this specification, the following abbreviations shall have the following meanings, unless the context clearly indicates otherwise: A=amperes; A/dm$^2$=amperes per square decimeter; ° C.=degrees Centigrade; g=gram; mg=milligram; L=liter; L/m=liters per minute; ppm=parts per million; μm=micron=micrometer; mm=millimeters; cm=centimeters; DI=deionized; and mL=milliliter. All amounts are percent by weight and all ratios are molar ratios, unless otherwise noted. All numerical ranges are inclusive and combinable in any order, except where it is clear that such numerical ranges are constrained to add up to 100%.

As used throughout the specification, "feature" refers to the geometries on a substrate. "Apertures" refer to recessed features including through-holes and blind vias. As used throughout this specification, the term "plating" refers to metal electroplating. "Deposition" and "plating" are used interchangeably throughout this specification. "Halide" refers to fluoride, chloride, bromide and iodide. Likewise, "halo" refers to fluoro, chloro, bromo and iodo. The term "alkyl" includes linear, branched and cyclic alkyl. "Accelerator" refers to an organic additive that increases the plating rate of the electroplating bath. A "suppressor" refers to an organic additive that suppresses the plating rate of a metal during electroplating. "Leveler" refers to an organic compound that is capable of providing a substantially level (or planar) metal layer. The terms "leveler" and "leveling agent" are used interchangeably throughout this specification. The terms "printed circuit boards" and "printed wiring boards" are used interchangeably throughout this specification. The articles "a" and "an" refer to the singular and the plural.

The plating bath and method of the present invention are useful in providing a substantially level plated copper layer on a substrate, such as a printed circuit board. Also, the present invention is useful in filling apertures in a substrate with copper. Such filled apertures are substantially free of voids. Also, the copper deposits from the present invention are substantially free of nodules, that is, they contain ≦15 nodules/95 cm$^2$ surface area.

Any substrate upon which copper can be electroplated is useful in the present invention. Such substrates include, but are not limited to, electronic devices such as printed wiring boards, integrated circuits, semiconductor packages, lead frames and interconnects. It is preferred that the substrate is a PCB or an integrated circuit. In one embodiment, the integrated circuit substrate is a wafer used in a dual damascene manufacturing process. Such substrates typically contain a number of features, particularly apertures, having a variety of sizes. Through-holes in a PCB may have a variety of diameters, such as from 50 μm to 150 μm in diameter. Such through-holes may vary in depth, such as from 35 μm to 100 μm. PCBs may contain blind vias having a wide variety of sizes, such as up to 200 μm, or greater. The present invention is particularly suitable for filling apertures, of varying aspect ratios, such as low aspect ratio vias and high aspect ratio apertures. By "low aspect ratio" is meant an aspect ratio of from 0.1:1 to 4:1. The term "high aspect ratio" refers to aspect ratios of greater than 4:1, such as 10:1 or 20:1.

The copper plating baths of the present invention contain a source of copper ions, an electrolyte, and a leveling agent, wherein the leveling agent is a reaction product of one or more benzimidazole compounds with one or more epoxide-containing compounds; wherein at least one benzimidazole compound has the formula

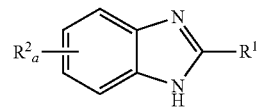

wherein $R^1$ is selected from H, $(C_1-C_6)$alkyl, ar$(C_1-C_6)$alkyl, hydroxy$(C_1-C_6)$alkyl and hydroxy; each $R^2$ is independently selected from $(C_6-C_{18})$aryl, $(C_1-C_6)$alkyl, ar$(C_1-C_6)$alkyl, hydroxy$(C_1-C_6)$alkyl and hydroxy; and a=0-4, provided that a>0 when $R^1$=H. The copper plating baths also typically contain a source of halide ions, an accelerator and a suppressor.

Any copper ion source that is at least partially soluble in the electroplating bath is suitable. Preferably, the copper ion source is soluble in the plating bath. Suitable copper ion sources are copper salts and include without limitation: copper sulfate; copper halides such as copper chloride; copper acetate; copper nitrate; copper fluoroborate; copper alkylsulfonates; copper arylsulfonates; copper sulfamate; and copper gluconate. Exemplary copper alkylsulfonates include copper $(C_1-C_6)$alkylsulfonate and more preferably copper $(C_1-C_3)$ alkylsulfonate. Preferred copper alkylsulfonates are copper methanesulfonate, copper ethanesulfonate and copper propanesulfonate. Exemplary copper arylsulfonates include, without limitation, copper phenyl sulfonate, copper phenol sulfonate and copper p-toluene sulfonate. Copper sulfate pentahydrate and copper methanesulfonic acid are preferred. Mixtures of copper ion sources may be used. It will be appreciated by those skilled in the art that one or more salts of metal ions other than copper ions may be advantageously added to the present electroplating baths. The addition of such other metal ion sources are useful in the deposition of copper alloys. Such copper salts are generally commercially available and may be used without further purification.

The copper salts may be used in the present plating baths in any amount that provides sufficient copper ion concentration for electroplating copper on a substrate. Typically, the copper salt is present in an amount sufficient to provide an amount of copper metal of 10 to 180 g/L of plating solution. Alloys, such as copper-tin, for example, copper having up to 2% by weight tin, may be advantageously plated according to the present invention. Other suitable copper alloys include, but are not limited to copper-silver, tin-copper-silver, and tin-copper-bismuth. The amount of each of the metal salts in such mixtures depends upon the particular alloy to be plated and is well known to those skilled in the art.

The electrolyte useful in the present invention may be alkaline or acidic. Suitable acidic electrolytes include, but are not limited to, sulfuric acid, acetic acid, fluoroboric acid, alkanesulfonic acids such as methanesulfonic acid, ethanesulfonic acid, propanesulfonic acid and trifluoromethane sulfonic acid, arylsulfonic acids such as phenyl sulfonic acid, phenol sulfonic acid and toluene sulfonic acid, sulfamic acid, hydrochloric acid, and phosphoric acid. Mixtures of acids may be advantageously used in the present metal plating baths. Preferred acids include sulfuric acid, methanesulfonic acid, ethanesulfonic acid, propanesulfonic acid, and mixtures thereof. The acids are typically present in an amount in the range of from 1 to 300 g/L, more typically from 5 to 250 g/L, and still more typically from 10 to 250 g/L. Electrolytes are generally commercially available from a variety of sources and may be used without further purification.

Such electrolytes may optionally contain a source of halide ions. Chloride ions are the preferred halide ions. Exemplary chloride ion sources include copper chloride and hydrochloric acid. A wide range of halide ion concentrations may be used in the present invention. Typically, the halide ion concentration is in the range of from 0 to 100 ppm based on the plating bath, and preferably from 10 to 100 ppm. A particularly useful amount of halide ion is 20 to 75 ppm. Such halide ion sources are generally commercially available and may be used without further purification.

The present plating baths typically contain an accelerator. Any accelerators (also referred to as brightening agents) are suitable for use in the present invention. Such accelerators are well-known to those skilled in the art. Typical accelerators contain one or more sulfur atoms and have a molecular weight of 1000 or less. Accelerator compounds that have sulfide and/or sulfonic acid groups are generally preferred, particularly compounds that include a group of the formula R'—S—R—SO$_3$X, where R is optionally substituted alkyl, optionally substituted heteroalkyl, optionally substituted aryl, or optionally substituted heterocyclic; X is a counter ion such as sodium or potassium; and R' is hydrogen or a chemical bond. Typically, the alkyl groups are $(C_1-C_{16})$alkyl and preferably $(C_3-C_{12})$alkyl. Heteroalkyl groups typically have one or more heteroatoms, such as nitrogen, sulfur or oxygen, in the alkyl chain. Suitable aryl groups include, but are not limited to, phenyl, benzyl, biphenyl and naphthyl. Suitable heterocyclic groups typically contain from 1 to 3 heteroatoms, such as nitrogen, sulfur or oxygen, and 1 to 3 separate or fused ring systems. Such heterocyclic groups may be aromatic or non-aromatic. Preferred accelerators for use in the present invention include: N,N-dimethyl-dithiocarbamic acid-(3-sulfopropyl)ester; 3-mercapto-propylsulfonic acid-(3-sulfopropyl) ester; 3-mercapto-propylsulfonic acid sodium salt; carbonic acid-dithio-o-ethylester-s-ester with 3-mercapto-1-propane sulfonic acid potassium salt; bis-sulfopropyl disulfide; 3-(benzothiazolyl-s-thio)propyl sulfonic acid sodium salt; pyridinium propyl sulfobetaine; 1-sodium-3-mercaptopropane-1-sulfonate; N,N-dimethyl-dithiocarbamic acid-(3-sulfoethyl)ester; 3-mercapto-ethyl propylsulfonic acid-(3-sulfoethyl)ester; 3-mercapto-ethylsulfonic acid sodium salt; carbonic acid-dithio-o-ethylester-s-ester with 3-mercapto-1-ethane sulfonic acid potassium salt; bis-sulfoethyl disulfide; 3-(benzothiazolyl-s-thio)ethyl sulfonic acid sodium salt; pyridinium ethyl sulfobetaine; and 1-sodium-3-mercaptoethane-1-sulfonate.

Such accelerators may be used in a variety of amounts. In general, accelerators are used in an amount of at least 0.01 mg/L, based on the bath, preferably at least 0.5 mg/L, and more preferably at least 1 mg/L. For example, the accelerators are present in an amount of from 0.1 mg/L to 200 mg/L. The particular amount of accelerator will depend upon the specific application, such as high aspect ratio, through-hole filling, and via filling applications. Preferable amounts of accelerator useful in the present invention are at least 0.5 mg/L, and more preferably at least 1 mg/L. A preferable range of such accelerator concentrations is from 0.1 to 10 mg/L (ppm).

Any compound capable of suppressing the copper plating rate may be used as a suppressor in the present electroplating baths. Suitable suppressors include, but are not limited to, polymeric materials, particularly those having heteroatom substitution, and more particularly oxygen substitution. Exemplary suppressors are high molecular weight polyethers, such as those of the formula R—O—(CXYCX'Y'O)$_n$R' where R and R' are independently chosen from H, $(C_2-C_{20})$alkyl group and $(C_6-C_{10})$aryl group; each of X, Y, X' and Y' is independently selected from hydrogen, alkyl such as methyl, ethyl or propyl, aryl such as phenyl, or aralkyl such as benzyl; and n is an integer from 3 to 10,000. Typically, one or more of X, Y, X' and Y' is hydrogen. Preferred suppressors include commercially available polypropylene glycol copolymers and polyethylene glycol copolymers, including ethylene oxide-propylene oxide ("EO/PO") copolymers and butyl alcohol-ethylene oxide-propylene oxide copolymers. Suitable butyl alcohol-ethylene oxide-propylene oxide copolymers are those having a weight average molecular weight of 500 to 10,000, and preferably 1000 to 10,000. When such suppressors are used, they are typically present in an amount in the range of from 1 to 10,000 ppm based on the weight of the bath, and preferably from 5 to 10,000 ppm.

The reaction products of the present invention contain at least one benzimidazole compound of the formula

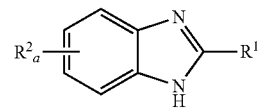

wherein $R^1$ is selected from H, $(C_1-C_6)$alkyl, ar$(C_1-C_6)$alkyl, hydroxy$(C_1-C_6)$alkyl and hydroxy; each $R^2$ is independently selected from $(C_6-C_{18})$aryl, $(C_1-C_6)$alkyl, ar$(C_1-C_6)$alkyl, hydroxy$(C_1-C_6)$alkyl and hydroxy; and a=0-4, provided that a>0 when $R^1$=H. Preferably, $R^1$ is selected from H, $(C_1-C_4)$ alkyl, ar$(C_1-C_4)$alkyl, and hydroxy$(C_1-C_4)$alkyl, and more preferably H, methyl, ethyl, propyl, butyl, benzyl, hydroxymethyl and hydroxyethyl. $R^2$ is preferably selected from $(C_6-C_{18})$aryl, $(C_1-C_4)$alkyl, ar$(C_1-C_4)$alkyl, and hydroxy$(C_1-C_4)$ alkyl. More preferably, $R^2$ is selected from phenyl, tolyl, xylyl, naphthyl, ethylphenyl, methyl, ethyl, propyl, butyl, benzyl, phenethyl, naphthylmethyl, hydroxymethyl and hydroxyethyl. It is further preferred that $R^2$ is selected from phenyl, tolyl, methyl, ethyl, propyl, butyl, benzyl, phenethyl, and hydroxymethyl. It is preferred that a=0-3, and more preferably a=0-2, and still more preferably a=1-2. Particularly preferred benzimidazoles are those where $R^1$ is selected from H, methyl, ethyl, butyl, benzyl, and hydroxymethyl; $R^2$ is selected from methyl, ethyl, butyl, phenyl, benzyl and hydroxymethyl; and a=0-2. It will be appreciated by those skilled in the art that the present benzimidazole compounds are substituted, that is, they exclude benzimidazole itself. The benzimidazole compounds useful in the present invention are generally commercially available from a variety of sources, such as Sigma-Aldrich (St. Louis, Mo.) or may be prepared from literature methods.

Any suitable epoxide-containing compound may be used to make the reaction products of the present invention. Such epoxide-containing compounds may contain 1 or more epoxide groups, and typically contain 1, 2 or 3 epoxide groups, and preferably contain 1 or 2 epoxide groups. Suitable epoxide-containing compounds useful in the present invention are those of the formulae E-I, E-II, or E-III

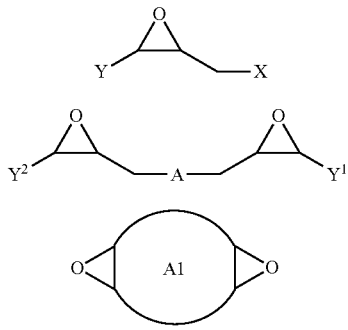

where Y, $Y^1$ and $Y^2$ are independently chosen from H and $(C_1-C_4)$alkyl; X=halogen; A=$OR^4$ or $R^5$; $R^4$=$((CR^6R^7)_mO)_n$, (aryl-O)$_p$, $CR^6R^7$—Z—$CR^6R^7O$ or $OZ^1_tO$; $R^5$=$(CH_2)_y$; $A^1$ is $(C_5-C_{12})$cycloalkyl; Z=a 5- or 6-membered ring; $Z^1$ is $R^{12}OArOR^{12}$, $(R^{13}O)_aAr(OR^{13})_a$, or $(R^{13}O)_aCy(OR^{13})_a$; Cy=$(C_5-C_{12})$cycloalkyl; each $R^6$ and $R^7$ are independently chosen from H, $CH_3$ and OH; each $R^{11}$ represents $(C_1-C_4)$ alkyl or $(C_1-C_4)$alkoxy; each $R^{12}$ represents $(C_1-C_8)$alkyl; each $R^{13}$ represents a $(C_2-C_6)$alkyleneoxy; each a=1-10; m=1-6; n=1-20; p=1-6; q=1-6; r=0-4; t=1-4; and y=0-6; wherein Y and $Y^1$ may be taken together to form a $(C_8-C_{12})$ cyclic compound. Preferably Y=H and X=Cl or Br, and more preferably, X=Cl. $Y^1$ and $Y^2$ are preferably independently chosen from H and $(C_1-C_2)$alkyl. When $Y^1$ and $Y^2$ are not joined to form a cyclic compound, it is preferred that $Y^1$ and $Y^2$ are both H. When $Y^1$ and $Y^2$ are joined to form a cyclic compound, it is preferred that A is $R^5$ or a chemical bond and that a $(C_8-C_{10})$carbocyclic ring is formed. It is preferred that m=2-4. Preferably, n=1-10. It is further preferred that m=2-4 when n=1-10. Phenyl-O is the preferred aryl-O group for $R^4$. It is preferred that p=1-4, more preferably 1-3, and still more preferably 1-2. Z is preferably a 5- or 6-membered carbocyclic ring and, more preferably, Z is a 6-membered carbocyclic ring. Preferably, y=0-4, and more preferably 1-4. When A=$R^5$ and y=0, then A is a chemical bond. Preferably, m=1-6, and more preferably 1-4. It is preferred that q=1-4, more preferably 1-3, and still more preferably 1-2. Preferably, r=0 and q=1, and more preferably $Y^1$ and $Y^2$=H, r=0 and q=1. Preferably, $Z^1$=$R^{12}OArOR^{12}$ or $(R^{13}O)_aAr(OR^{13})_a$. Each $R^{12}$ is preferably $(C_1-C_6)$alkyl and more preferably $(C_1-C_4)$alkyl. Each $R^{13}$ is preferably $(C_2-C_4)$alkyleneoxy. It is preferred that t=1-2. Preferably, a=1-8, more preferably 1-6 and still more preferably 1-4.

Exemplary epoxide-containing compounds of formula E-I are epihalohydrins. Preferably, the epoxide-containing compound is epichlorohydrin or epibromohydrin, and more preferably, epichlorohydrin.

Suitable compounds of formula E-II where $R^4$=$((CR^6R^7)_mO)_n$ are those of the formula:

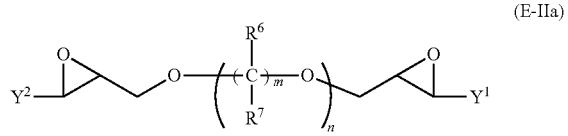

where $Y^1$, $Y^2$, $R^6$, $R^7$, n and m are as defined above. Preferably, $Y^1$ and $Y^2$ are both H. When m=2, it is preferred that each $R^6$ is H, $R^7$ is chosen from H and $CH_3$, and n=1-10. When m=3, it is preferred that at least one $R^7$ is chosen from $CH_3$ and OH, and n=1. When m=4, it is preferred that both $R^6$ and $R^7$ are H, and n=1. Exemplary compounds of formula E-IIa include, but are not limited to: 1,4-butanediol diglycidyl ether, ethylene glycol diglycidyl ether, di(ethylene glycol) diglycidyl ether, poly(ethylene glycol) diglycidyl ether compounds, glycerol diglycidyl ether, neopentyl glycol diglycidyl ether, propylene glycol diglycidyl ether, di(propylene glycol) diglycidyl ether, and poly(propylene glycol) diglycidyl ether compounds. Poly(ethylene glycol) diglycidyl ether compounds of formula E-IIa are those compounds where each of $R^6$ and $R^7$=H, m=2, and n=3-20, and preferably n=3-15, more preferably n=3-12, and still more preferably n=3-10. Exemplary poly(ethylene glycol) diglycidyl ether compounds include tri(ethylene glycol) diglycidyl ether, tetra(ethylene glycol) diglycidyl ether, penta(ethylene glycol) diglycidyl ether, hexa(ethylene glycol) diglycidyl ether, nona(ethylene glycol) diglycidyl ether, deca(ethylene glycol) diglycidyl ether, and dodeca(ethylene glycol) diglycidyl ether. Polypropylene glycol) diglycidyl ether compounds of formula E-IIa are those compounds where each of $R^6$=H and one of $R^7$=$CH_3$, m=2, and n=3-20, and preferably n=3-15, more preferably n=3-12, and still more preferably n=3-10. Exemplary poly(propylene glycol) diglycidyl ether compounds include tri(propylene glycol) diglycidyl ether, tetra(propylene glycol) diglycidyl ether, penta(propylene glycol) diglycidyl ether, hexa(propylene glycol) diglycidyl ether, nona(propylene glycol) diglycidyl ether, deca (propylene glycol) diglycidyl ether, and dodeca(propylene glycol) diglycidyl ether. Suitable poly(ethylene glycol) diglycidyl ether compounds and poly(propylene glycol) diglycidyl ether compounds are those having a number average molecular weight of from 350 to 10000, and preferably from 380 to 8000.

Suitable compounds of formula E-II where $R^4$=(aryl-O)$_p$ are those having the formulae E-IIb and E-IIc:

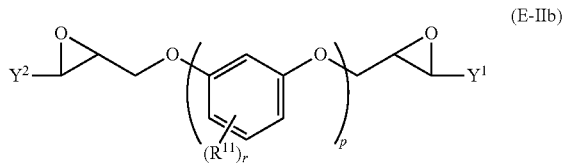

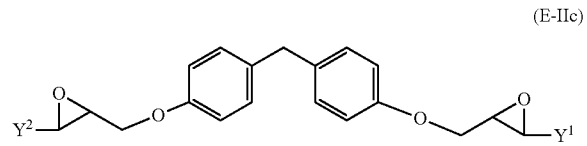

where $Y^1$, $Y^2$ and p are as defined above, and each $R^{11}$ represents $(C_1-C_4)$alkyl or $(C_1-C_4)$alkoxy, and r=0-4. Preferably, r=0 and p=1, and more preferably $Y^1$ and $Y^2$=H, r=0 and p=1.

In compounds of formula E-II where $R^4$=$CR^6R^7$—Z—$CR^6R^7O$, Z represents a 5- or 6-membered ring. In such ring structures, the $CR^6R^7$ groups may be attached at any position, such as at adjacent atoms of the ring or at any other atoms of the ring. Particularly suitable compounds of formula E-II where $R^4$=$CR^6R^7$—Z—$CR^6R^7O$ are those having the formula

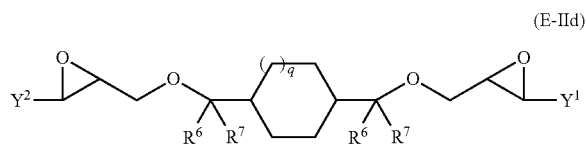

(E-IId)

where $Y^1$, $Y^2$, $R^6$ and $R^7$ are as defined above, and q=0 or 1. When q=0, the ring structure is a 5-membered carbocyclic ring and when q=1, the ring structure is a 6-membered carbocyclic ring. Preferably, $Y^1$ and $Y^2$=H. More preferably, $Y^1$ and $Y^2$=H and q=1. Preferred compounds of formula E-II where $R^4$=$CR^6R^7$—Z—$CR^6R^7O$ are 1,2-cyclohexanedimethanol diglycidyl ether and 1,4-cyclohexanedimethanol diglycidyl ether.

When A=$R^5$, suitable compounds of formula E-H are those having the formula:

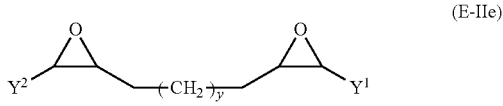

(E-IIe)

where $Y^1$, $Y^2$ and y are as defined above. It is preferred that y=0-4, more preferably y=1-4, and y=2-4. Exemplary compounds of formula E-IIe include, without limitation, 1,5-diepoxyhexane, 1,7-diepoxyoctane, and 1,9-diepoxydecane.

In compounds of formula II where A=$OZ^1_rO$, preferred compounds are those of the formula

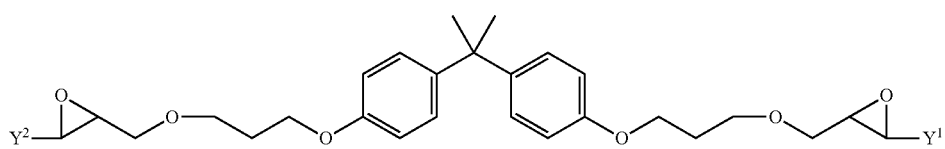

(E-IIf)

wherein $Y^1$ and $Y^2$ are as defined above.

Suitable epoxy-containing compounds of formula E-III may be monocyclic, spirocyclic, fused and/or bicyclic rings. Preferred epoxide-containing compounds of formula E-III include 1,5-diepoxy-cyclooctane, 1,6-diepoxy-cyclodecane and dicyclopentadiene dioxide.

The epoxide-containing compounds useful in the present invention can be obtained from a variety of commercial sources, such as Sigma-Aldrich, or can be prepared using a variety of literature methods known in the art.

The reaction products of the present invention can be prepared by reacting one or more benzimidazole compounds described above with one or more epoxide-containing compounds described above. Typically, a desired amount of the benzimidazole and epoxy-containing compounds were added into the reaction flask, followed by addition of water. The resulting mixture is heated to approximately to 75-95° C. for 4 to 6 hours. After an additional 6-12 hours of stirring at room temperature, the resulting reaction product is diluted with water. The reaction product may be used as-is in aqueous solution, may be purified or may be isolated as desired.

In general, the present reaction products have a number average molecular weight (Mn) of 500 to 10,000, although reaction products having other Mn values may be used. Such reaction products may have a weight average molecular weight (Mw) value in the range of 1000 to 50,000, although other Mw values may be used. Typically, Mw is from 1000 to 20,000. In one embodiment, Mw is 1500 to 5000. In another embodiment, Mw is 5000 to 15,000.

Typically, the ratio of the one or more benzimidazole compound to the one or more epoxide-containing compound is from 0.1:10 to 10:0.1. Preferably, the ratio is from 0.5:5 to 5:0.5 and more preferably from 0.5:1 to 1:0.5. Other suitable ratios of the one or more benzimidazole compounds to the one or more epoxide-containing compounds may be used to prepare the present leveling agents.

It will be appreciated by those skilled in the art that a reaction product of the present invention may also possess functionality capable of acting as a suppressor. Such compounds may be dual-functioning, i.e. they may function as leveling agents and as suppressors.

The amount of the reaction product (leveling agent) used in the metal electroplating baths will depend upon the particular leveling agents selected, the concentration of the metal ions in the electroplating bath, the particular electrolyte used, the concentration of the electrolyte and the current density applied. In general, the total amount of the leveling agent in the electroplating bath is from 0.01 ppm to 5000 ppm based on the total weight of the plating bath, although greater or lesser amounts may be used. Preferably, the total amount of the leveling agent is from 0.25 to 5000 ppm, more preferably from 0.25 to 1000 ppm and still more preferably from 0.25 to 100 ppm.

The leveling agents of the present invention may possess any suitable molecular weight polydispersity. The present leveling agents work over a wide molecular weight polydispersity range.

The electroplating baths of the present invention are typically aqueous. Unless otherwise specified, all concentrations of components are in an aqueous system. Particularly suitable compositions useful as electroplating baths in the present invention include a soluble copper salt, an acid electrolyte, an accelerator, a suppressor, halide ion and a reaction product described above as a leveling agent. More preferably, suitable compositions include 10 to 220 g/L of a soluble copper salts as copper metal, 5 to 250 g/L of acid electrolyte, 1 to 50 mg/L of an accelerator, 1 to 10,000 ppm of a suppressor, 10 to 100 ppm of a halide ion, and 0.25 to 5000 ppm of a reaction product described above as a leveling agent.

The electroplating baths of the present invention may be prepared by combining the components in any order. It is preferred that the inorganic components such as source of copper ions, water, electrolyte and optional halide ion source, are first added to the bath vessel followed by the organic components such as leveling agent, accelerator, suppressor, and any other organic component.

The present electroplating baths may optionally contain a second leveling agent. Such second leveling agent may be another leveling agent of the present invention, or alternatively, may be any conventional leveling agent. Suitable conventional leveling agents that can be used in combination with the present leveling agents include, without limitations, those disclosed in U.S. Pat. Nos. 6,610,192 (Step et al.), 7,128,822 (Wang et al.), 7,374,652 (Hayashi et al.), and 6,800,188 (Hagiwara et al.). Such combination of leveling agents may be used to tailor the characteristics of the plating bath, including leveling ability, throwing power and nodule reduction.

The plating baths of the present invention may be used at any suitable temperature, such as from 10 to 65° C. or higher. Preferably, the temperature of the plating baths is from 10 to 35° C. and still more preferably from 15 to 30° C.

In general, the present copper electroplating baths are agitated during use. Any suitable agitation method may be used with the present invention and such methods are well-known in the art. Suitable agitation methods include, but are not limited to, air sparging, work piece agitation, and impingement.

Typically, a substrate is electroplated by contacting the substrate with the plating bath of the present invention. The substrate typically functions as the cathode. The plating bath contains an anode, which may be soluble or insoluble. Potential is typically applied to the cathode. Sufficient current density is applied and plating performed for a period of time sufficient to deposit a copper layer having a desired thickness on the substrate as well as fill blind vias and/or through holes. Suitable current densities, include, but are not limited to, the range of 0.05 to 10 A/dm$^2$, although higher and lower current densities may be used. The specific current density depends in part upon the substrate to be plated and the leveling agent selected. Such current density choice is within the abilities of those skilled in the art.

The present invention is useful for depositing a copper layer on a variety of substrates, particularly those having variously sized apertures. Accordingly, the present invention provides a method of depositing a copper layer on a substrate including the steps of: contacting a substrate to be plated with copper with the copper plating bath described above; and then applying a current density for a period of time sufficient to deposit a copper layer on the substrate. For example, the present invention is particularly suitable for depositing copper on printed circuit boards with blind vias and through-holes.

Copper is deposited in apertures according to the present invention without substantially forming voids within the metal deposit. By the term "without substantially forming voids", it is meant that >95% of the plated apertures are void-free. It is preferred that the plated apertures are void-free. Copper is also deposited uniformly in through-holes and in high aspect ratio through-holes with improved throwing power, surface distribution and thermal reliability.

While the process of the present invention has been generally described with reference to printed circuit board manufacture, it will be appreciated that the present invention may be useful in any electrolytic process where an essentially level or planar copper deposit and filed apertures that are substantially free of voids are desired. Such processes include semiconductor packaging and interconnect manufacture.

An advantage of the present invention is that substantially level copper deposits are obtained on a PCB. By "substantially level" copper layer is meant that the step height, that is, the difference between areas of dense very small apertures and areas free of or substantially free of apertures, is less than 5 µm, and preferably less than 1 µm. Through-holes and/or blind vias in the PCB are substantially filled with substantially no void formation. A further advantage of the present invention is that a wide range of apertures and aperture sizes may be filled within a single substrate with substantially no suppressed local plating. Thus, the present invention is particularly suitable for filling blind vias and/or through-holes in a printed circuit board, where such blind vias and through-holes are substantially free of added defects. "Substantially free of added defects" refers to the leveling agent not increasing the number or size of defects, such as voids, in filled apertures as compared to control plating baths not containing such leveling agent. A further advantage of the present invention is that a substantially planar copper layer may be deposited on a PCB having non-uniformly sized apertures. "Non-uniformly sized apertures" refer to apertures having a variety of sizes in the same PCB.

Throwing power is defined as the ratio of the average thickness of the metal plated in the center of a through-hole compared to the average thickness of the metal plated at the surface of the PCB sample and is reported as a percentage. The higher the throwing power, the better the plating bath is able to fill the through-hole. Copper plating baths of the present invention have a throwing power of $\geq$70%, preferably $\geq$75%, and more preferably $\geq$80%. Copper plating baths of the present invention also show reduced nodule formation on a copper plated substrate as compared to conventional copper plating baths. Preferably, the present copper plating baths provide copper deposits having $\leq$15 nodules per 95 cm$^2$ surface area, more preferably $\leq$10 nodules per 95 cm$^2$, and still more preferably $\leq$8 nodules per 95 cm$^2$. In addition, the copper plating baths of the present invention provide copper deposits having reduced cracking. Preferably, the present copper plating baths provide copper deposits showing $\leq$10% cracking, more preferably $\leq$8% cracking, and even more preferably $\leq$5% cracking. The throwing power, amount of nodules formed and percentage cracking are all determined as described in Example 5.

EXAMPLE 1

2-Methylbenzimidazole (150 mmol) and 94.5 mmole of 1,4-butanediol diglycidyl ether were added at room temperature to a round-bottom reaction flask equipped with a condenser, thermometer and set in a heating bath. Then, 30 mL of DI water were added to the flask. The initially formed white colored suspension eventually disappeared as the reaction temperature increased and turned into a phase separated mixture. The reaction mixture was heated for 1.5 hours using an oil bath set to 98° C. After adding 2 mL of concentrated sulfuric acid into the reaction flask, the solution became transparent with a light-yellow color. The mixture was heated for an additional 4 hours and left stirring at room temperature for another 8 hours. Concentrated sulfuric acid (2 mL) was added to the resulting white colored solid reaction product and transferred into a volumetric flask, rinsed and diluted with 0.5-1% sulfuric acid to form a light beige colored solution. The reaction product (Reaction Product 3, see Table 1) solution was used without further purification.

EXAMPLE 2

Example 1 was repeated except that the benzimidazoles in Table 1 were used. The molar ratio of benzimidazole compound to epoxide-containing compound for each reaction product was 1:0.63. The UV-absorption of the reaction products was determined in water using an Agilent 8453 spectrophotometer and the $\lambda_{max}$ (nm) is reported in the following table.

TABLE 1

| Reaction Product | Benzimidazole compound | Epoxide-containing compound | $\lambda_{max}$ (nm) |
| --- | --- | --- | --- |
| 1 | 5,6-dimethylbenzimidazole | diglycidyl ether of 1,4-butanediol | 195, 278, 286 |
| 2 | 5-methylbenzimidazole | diglycidyl ether of 1,4-butanediol | 194, 257, 275, 283 |
| 3 | 2-methylbenzimidazole | diglycidyl ether of 1,4-butanediol | 243, 269, 276 |
| 4 | 2,5-dimethylbenzimidazole | diglycidyl ether of 1,4-butanediol | 196, 246, 276, 283 |
| 5 | 2-hydroxymethylbenzimidazole | diglycidyl ether of 1,4-butanediol | 200, 255, 269, 276 |

EXAMPLE 3

Example 1 is repeated except that the benzimidazoles and epoxide-containing compounds listed in Table 2 are used. The molar ratios of benzimidazole compound: epoxide-containing compound in the expected reaction products are also listed in Table 2.

EXAMPLE 4

Various copper plating baths were prepared by combining 75 g/L copper as copper sulfate pentahydrate, 240 g/L sulfuric acid, 60 ppm chloride ion, 1-2 ppm of an accelerator and 1.5 g/L of a suppressor. The accelerator was a disulfide compound having sulfonic acid groups and a molecular weight of <1000. The suppressor was an EO/PO copolymer having a molecular weight of <5,000 and terminal hydroxyl groups. Each plating bath also contained from 1-15 ppm of a reaction product from Examples 1 or 2.

EXAMPLE 5

Samples (3.2 mm thick) of a double-sided FR4 PCB (5×9.5 cm) having through-holes (0.3 mm diameter) were plated using copper plating baths according to Example 4 in a Haring cell. The temperature of the baths was 25° C. A current density of 2.2 A/dm² (20 A/ft²) was applied to each bath for 80 minutes. The copper plated samples were analyzed to determine the throwing power ("TP") of the plating bath, nodule formation, and percent cracking according to the following methods. Analysis of the samples showed that copper plating bath using each of reaction products 1-5 showed very good throwing power (>70%) and showed a low number of nodules.

TABLE 2

| Reaction Product | Monomer 1 | Monomer 2 | Monomer 3 | Molar ratio M1:M2:M3 |
| --- | --- | --- | --- | --- |
| 6 | 5-methylbenzimidazole | 4-methylimidazole | epichlorohydrin | 1:1:1.2 |
| 7 | 5-methylbenzimidazole | diglycidyl ether of 1,4-butanediol | epichlorohydrin | 2:1:1.2 |

TABLE 2-continued

| Reaction Product | Monomer 1 | Monomer 2 | Monomer 3 | Molar ratio M1:M2:M3 |
|---|---|---|---|---|
| 8 | 5-ethyl-1H-benzimidazole | diglycidyl ether of glycerol | | 1:0.63 |
| 9 | 2-methyl-1H-benzimidazole | 2,2-dimethyl-1,3-propanediol diglycidyl ether | | 1:0.5 |
| 10 | 2-methyl-1H-benzimidazole | epichlorohydrin | | 1:2 |
| 11 | 2-hydroxy-1H-benzimidazole | 1,4-butanediol diglycidyl ether | | 1:0.63 |
| 12 | 2-hydroxy-1H-benzimidazole | ethylene glycol diglycidyl ether | | 1:0.75 |
| 13 | 2-ethyl-1H-benzimidazole | 1,2,7,8-diepoxyoctane | | 1:0.63 |
| 14 | 2-ethyl-1H-benzimidazole | 4-phenyl-1H-imidazole | diglycidyl ether of glycerol | 3:1:2.4 |
| 15 | 2-(hydroxymethyl)-1H-benzimidazole | 1H-imidazole | 1,2:5,6-diepoxycyclooctane | 1:3:2.6 |
| 16 | 2-(hydroxymethyl)-1H-benzimidazole | 1H-imidazole | 1,2:5,6-diepoxycyclooctane | 1:1:2.6 |
| 17 | 2,5-dimethyl-1H-benzimidazole | 1,2,5,6-diepoxyhexane | | 1:1 |
| 18 | 5,6-dimethyl-1H-benzimidazole | 1,4-butanediol diglycidyl ether | epichlorohydrin | 1:0.5:0.6 |

TABLE 2-continued

| Reaction Product | Monomer 1 | Monomer 2 | Monomer 3 | Molar ratio M1:M2:M3 |
|---|---|---|---|---|
| 19 | (2-benzyl benzimidazole structure) | (diepoxide structure) | | 1:0.63 |

EXAMPLE 6

Comparative

A conventional leveling agent, comparative reaction product C-1, shown in Table 3 was prepared according to the procedure of Example 1.

TABLE 3

| Comparative Reaction Product | Monomer 1 (M1) | Monomer 2 (M2) | Molar ratio M1:M2 |
|---|---|---|---|
| C-1 | (benzimidazole structure) | (bis-epoxide ether structure) | 1:0.63 |

EXAMPLE 7

Copper plating baths were prepared according to Example 4 except that 2 ppm of accelerator was used. Either 5 or 10 ppm of Reaction Product 3, 4 and C-1 were used as the leveling agent. Samples (3.2 mm thick) of a double-sided FR4 PCB (5×9.5 cm) having through-holes (0.3 mm diameter) were plated using these copper plating baths in a Haring cell. The temperature of the baths was 25° C. A current density of 2.2 A/dm$^2$ (20 A/ft$^2$) was applied to each bath for 80 minutes. The copper plated samples were analyzed to determine the throwing power ("TP") of the plating bath, nodule formation, and percent cracking according to the following methods. The data are reported in Table 4.

Throwing power was calculated by determining the ratio of the average thickness of the metal plated in the center of a through-hole compared to the average thickness of the metal plated at the surface of the PCB sample and is reported in Table 4 as a percentage.

Nodule formation was determined both by visual inspection and by using the Reddington Tactile Test ("RTT"). Visual inspection showed the presence of nodules while the RTT was used to determine the number of nodules. The RTT employs a person's finger to feel the number of nodules for a given area of the plated surface, which in this example was both sides of the PCB sample (total area of 95 cm$^2$).

The amount of cracking (reported in Table 4 as a percentage) was determined according to the industry standard procedure, IPC-TM-650-2.6.8. Thermal Stress, Plated-Through Holes, published by IPC (Northbrook, Ill., USA), dated May, 2004, revision E.

TABLE 4

| Reaction Product | Leveling Agent (ppm) | TP % | Nodules | Cracking (%) |
|---|---|---|---|---|
| C-1 | 5 | 86 | 0 | 8 |
| | 10 | 80 | 9 | 8 |
| 3 | 5 | 76 | 1 | 0 |
| | 10 | 82 | 1 | 0 |
| 4 | 5 | 73 | 3 | 0 |
| | 10 | 65 | 0 | 0 |

From these data, it can be seen that the present reaction products including a substituted benzimidazole provide copper plating baths having very good throwing power and provide copper deposits having reduced nodule formation and reduced cracking as compared to conventional reaction products used as leveling agents.

What is claimed is:

1. A copper electroplating bath comprising: a source of copper ions, an electrolyte, and a leveling agent, wherein the leveling agent is a reaction product of one or more benzimidazole compounds with one or more epoxide-containing compounds; wherein at least one benzimidazole compound has the formula

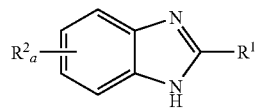

wherein $R^1$ is selected from H, $(C_1$-$C_3)$alkyl, ar$(C_1$-$C_3)$alkyl, hydroxy$(C_1$-$C_3)$alkyl and hydroxy; each $R^2$ is independently selected from $(C_6$-$C_{18})$aryl, $(C_1$-$C_3)$alkyl, ar$(C_1$-$C_3)$alkyl, hydroxy$(C_1$-$C_3)$alkyl and hydroxy; and a=0-4, provided that a >0 when $R^1$=H.

2. The copper electroplating bath of claim 1 wherein the epoxide-containing compound comprises from 1 to 3 epoxy groups.

3. The copper electroplating bath of claim 1 further comprising a second leveling agent.

4. A method of depositing copper on a substrate comprising: contacting a substrate to be plated with copper into the copper electroplating bath of claim 1; and applying a current density for a period of time sufficient to deposit a copper layer on the substrate.

5. The method of claim 4 wherein the substrate is a printed circuit board.

6. The copper electroplating bath of claim 1 wherein the source of copper ions is selected from copper sulfate, copper halides, copper acetate, copper nitrate, copper fluoroborate, copper alkylsulfonates, copper arylsulfonates, copper sulfamate, copper gluconate, and mixtures thereof.

7. The copper electroplating bath of claim 1 wherein the electrolyte is selected from sulfuric acid, acetic acid, fluoroboric acid, alkanesulfonic acids, arylsulfonic acids, sulfamic acid, hydrochloric acid, phosphoric acid and mixtures thereof.

8. The copper electroplating bath of claim 1 wherein the epoxide-containing compound is chosen from compounds of the formulae

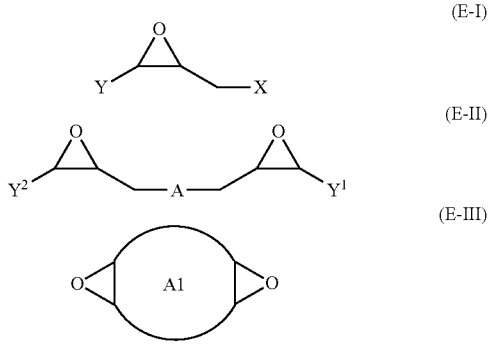

where Y, $Y^1$ and $Y^2$ are independently chosen from H and $(C_1-C_4)$alkyl; X=halogen; A=$OR^4$ or $R^5$; $R^4$=$((CR^6R^7)_mO)_n$, (aryl-O)$_p$, $CR^6R^7$—Z—$CR^6R^7O$ or $OZ^1_tO$; $R^5$=$(CH_2)_y$; A1 is $(C_5-C_{12})$cycloalkyl; Z=a 5- or 6-membered ring; $Z^1$ is $R^{12}OArOR^{12}$, $(R^{13}O)_aAr(OR^{13})_a$, or $(R^{13}O)_aCy(OR^{13})_a$; Cy=$(C_5-C_{12})$cycloalkyl; each $R^6$ and $R^7$ are independently chosen from H, $CH_3$ and OH; each $R^{11}$ represents $(C_1-C_4)$ alkyl or $(C_1-C_4)$alkoxy; each $R^{12}$ represents $(C_1-C_8)$alkyl; each $R^{13}$ represents a $(C_2-C_6)$alkyleneoxy; each a=1-10; m=1-6; n=1-20; p=1-6; q=1-6; r=0-4; t=1-4; and y=0-6; wherein Y and $Y^1$ may be taken together to form a $(C_8-C_{12})$ cyclic compound.

9. The copper electroplating bath of claim 8 wherein the epoxide-containing compound is chosen from epihalohydrins, 1,4-butanediol diglycidyl ether, ethylene glycol diglycidyl ether, di(ethylene glycol) diglycidyl ether, poly(ethylene glycol) diglycidyl ether compounds, glycerol diglycidyl ether, neopentyl glycol diglycidyl ether, propylene glycol diglycidyl ether, di(propylene glycol) diglycidyl ether, poly(propylene glycol) diglycidyl ether compounds, 1,2-cyclohexanedimethanol diglycidyl ether, 1,4-cyclohexanedimethanol diglycidyl ether, 1,5-diepoxyhexane, 1,7-diepoxyoctane, 1,9-diepoxydecane, 1,5-diepoxycyclooctane, 1,6-diepoxy-cyclodecane and dicyclopentadiene dioxide.

10. The copper electroplating bath of claim 1 wherein $R^1$ is chosen from H, $(C_1-C_4)$alkyl, ar$(C_1-C_4)$alkyl, and hydroxy$(C_1-C_4)$alkyl.

11. The copper electroplating bath of claim 1 wherein $R^2$ is chosen from $(C_6-C_{18})$aryl, $(C_1-C_4)$alkyl, ar$(C_1-C_4)$alkyl, and hydroxy$(C_1-C_4)$alkyl.

* * * * *